United States Patent
Sato et al.

(10) Patent No.: US 9,475,826 B2
(45) Date of Patent: Oct. 25, 2016

(54) FLUORINE-CONTAINING NANO COMPOSITE PARTICLES AND METHOD FOR PRODUCING THE SAME

(71) Applicants: UNIMATEC CO., LTD., Tokyo (JP); HIROSAKI UNIVERSITY, Aomori (JP)

(72) Inventors: Katsuyuki Sato, Ibaraki (JP); Hideo Sawada, Aomori (JP)

(73) Assignees: Unimatec Co., Ltd., Tokyo (JP); Hirosaki University, Aomori (JP)

( * ) Notice: Subject to any disclaimer, the term of this patent is extended or adjusted under 35 U.S.C. 154(b) by 0 days.

(21) Appl. No.: 14/773,172

(22) PCT Filed: Mar. 6, 2014

(86) PCT No.: PCT/JP2014/055819
§ 371 (c)(1),
(2) Date: Sep. 4, 2015

(87) PCT Pub. No.: WO2014/136894
PCT Pub. Date: Sep. 12, 2014

(65) Prior Publication Data
US 2016/0009739 A1    Jan. 14, 2016

(30) Foreign Application Priority Data

| Mar. 6, 2013 | (JP) | 2013-044084 |
| Mar. 6, 2013 | (JP) | 2013-044085 |
| Mar. 6, 2013 | (JP) | 2013-044086 |

(51) Int. Cl.
| C07F 7/08 | (2006.01) |
| C07F 7/02 | (2006.01) |
| C07C 31/38 | (2006.01) |
| C08G 77/18 | (2006.01) |
| C08G 77/24 | (2006.01) |
| C07C 29/149 | (2006.01) |

(52) U.S. Cl.
CPC .............. *C07F 7/025* (2013.01); *C07C 29/149* (2013.01); *C07C 31/38* (2013.01); *C08G 77/18* (2013.01); *C08G 77/24* (2013.01)

(58) Field of Classification Search
CPC .................................................... C07F 7/025
USPC ......................................................... 556/470
See application file for complete search history.

(56) References Cited

U.S. PATENT DOCUMENTS

| 3,574,770 A | 4/1971 | Paine et al. |
| 4,554,296 A | 11/1985 | Keil |
| 6,013,752 A | 1/2000 | Mowrer et al. |
| 2006/0111581 A1 | 5/2006 | Raab |
| 2009/0036706 A1 | 2/2009 | Murata et al. |
| 2009/0171127 A1 | 7/2009 | Murata et al. |
| 2010/0324205 A1 | 12/2010 | Maier et al. |

FOREIGN PATENT DOCUMENTS

| JP | 61-103930 | 5/1986 |
| JP | 05-186719 | 7/1993 |
| JP | 2002-514260 A | 5/2002 |
| JP | 2004-244428 A | 9/2004 |
| JP | 2004-285111 A | 10/2004 |
| JP | 2004285111 A | * 10/2004 |
| JP | 2006-143731 A | 6/2006 |
| JP | 2008-38015 A | 2/2008 |
| JP | 2008-514744 A | 5/2008 |
| JP | 4674604 | 2/2011 |
| JP | 2011-511113 A | 4/2011 |
| WO | WO 2006/032512 A3 | 3/2006 |
| WO | WO 2007/070949 A1 | 7/2007 |
| WO | WO 2007/105633 A1 | 9/2007 |
| WO | WO 2014136894 A1 | * 9/2014 ........... C07C 29/149 |

OTHER PUBLICATIONS

JP2004285111A, Chikada et al.—Translation.*
International Search Report (WO 2014/136894 A1); PCT/JP2014/055819.*
International Preliminary Report on Patentability and Written Opinion from corresponding PCT application No. PCT/JP2014/055819 dated Sep. 17, 2015 (7 pgs).
International Search Report from corresponding PCT application No. PCT/JP2014/055819 dated May 20, 2014 (4 pgs).

* cited by examiner

*Primary Examiner* — Porfirio Nazario Gonzalez
*Assistant Examiner* — Kofi Adzamli
(74) *Attorney, Agent, or Firm* — Brinks Gilson & Lione

(57) ABSTRACT

Fluorine-containing nano composite particles comprising a condensate of a fluorine-containing alcohol represented by the general formula:

$$R_F\text{-A-OH} \qquad [I]$$

wherein $R_F$ is a perfluoroalkyl group or a polyfluoroalkyl group in which some of the fluorine atoms of the perfluoroalkyl group are replaced by hydrogen atoms, and A is an alkylene group having 1 to 6 carbon atoms; and an alkoxysilane, or fluorine-containing nano composite particles comprising a condensate of a fluorine-containing alcohol represented by the general formula:

$$R_F'\text{-A-OH} \qquad [Ia]$$

or the general formula:

$$\text{HO-A-}R_F''\text{-A-OH} \qquad [Ib]$$

wherein $R_F'$ is a linear or branched perfluoroalkyl group containing an O, S, or N atom, $R_F''$ is a linear or branched perfluoroalkylene group containing an O, S, or N atom, and A is an alkylene group having 1 to 6 carbon atoms; and an alkoxysilane.

11 Claims, No Drawings

FLUORINE-CONTAINING NANO COMPOSITE PARTICLES AND METHOD FOR PRODUCING THE SAME

RELATED APPLICATION

This application is a 35 U.S.C. §371 national phase filing of International Patent Application No. PCT/JP2014/055819, filed Mar. 6, 2014, which claims priority under 35 U.S.C. §119 to Japanese Patent Application Nos. 2013-044084, filed Mar. 6, 2013, 2013-044085, filed Mar. 6, 2013, and 2013-044086, filed Mar. 6, 2013 the entire disclosure of each of which is hereby expressly incorporated by reference.

TECHNICAL FIELD

The present invention relates to fluorine-containing nano composite particles and a method for producing the same. More particularly, the present invention relates to fluorine-containing nano composite particles using a fluorine-containing alcohol, and a method for producing the same.

BACKGROUND ART

Patent Document 1 discloses a liquid, fluorine-containing and single-component composition for the permanent oil- and water-repellent surface treatment of porous and nonporous substrates, wherein the composition comprises a suitable stabilizing component and a hydrophilic silane component in combination, and has excellent storage stability, and hydrophobic, oleophobic and dust proof properties.

However, in the preparation of a surface treating agent for mineral and non-mineral substrates, a highly toxic isocyanate compound is used to introduce a silyl group into a fluorine compound. Therefore, its implementation requires the regulation of the production environment. Moreover, perfluorooctanoic acid and a fluorine-containing alcohol containing a perfluoroalkyl group having 8 or more carbon atoms, which is a precursor of perfluorooctanoic acid, are used, although less use of them is currently desired in terms of the current state of the environment.

PRIOR ART DOCUMENTS

Patent Documents

Patent Document 1: JP-A-2011-511113
Patent Document 2: JP-B-4674604
Patent Document 3: WO 2007/080949 A1
Patent Document 4: JP-A-2008-38015
Patent Document 5: U.S. Pat. No. 3,574,770

OUTLINE OF THE INVENTION

Problem to be Solved by the Invention

An object of the present invention is to provide fluorine-containing nano composite particles having excellent water- and oil-repellency, and using a fluorine-containing alcohol which does not produce perfluorooctanoic acid and the like, even when released into the environment, in the case of a perfluoroalkyl group having less than 8 carbon atoms, and to provide a method for producing the same.

Means for Solving the Problem

The present invention provides fluorine-containing nano composite particles comprising a condensate of a fluorine-containing alcohol represented by the general formula:

$$R_F\text{-A-OH} \quad [I]$$

wherein $R_F$ is a perfluoroalkyl group or a polyfluoroalkyl group in which some of the fluorine atoms of the perfluoroalkyl group are replaced by hydrogen atoms, and A is an alkylene group having 1 to 6 carbon atoms; and an alkoxysilane.

The fluorine-containing nano composite particles are produced by a method comprising subjecting the above fluorine-containing alcohol [I] and an alkoxysilane to a condensation reaction in the presence of an alkaline or acidic catalyst. The obtained fluorine-containing nano composite particles are used as an active ingredient of surface treating agents, such as water- and oil-repellents.

Moreover, the present invention provides fluorine-containing nano composite particles comprising a condensate of a fluorine-containing alcohol represented by the general formula:

$$R_F'\text{-A-OH} \quad [Ia]$$

or the general formula:

$$\text{HO-A-}R_F''\text{-A-OH} \quad [Ib]$$

wherein $R_F'$ is a linear or branched perfluoroalkyl group containing an O, S, or N atom, $R_F''$ is a linear or branched perfluoroalkylene group containing an O, S, or N atom, and A is an alkylene group having 1 to 6 carbon atoms; and an alkoxysilane.

The fluorine-containing nano composite particles are produced by a method comprising subjecting the above fluorine-containing alcohol [Ia] or [Ib] and an alkoxysilane to a condensation reaction in the presence of an alkaline or acidic catalyst. The obtained fluorine-containing nano composite particles are used as an active ingredient of surface treating agents, such as water- and oil-repellents.

Effect of the Invention

A thin film comprising the fluorine-containing nano composite particles according to the present invention not only has excellent water- and oil-repellency, but also can be stably dispersed in polar solvents such as water, alcohol, and tetrahydrofuran. The fluorine-containing nano composite particles also have excellent heat resistance at a high temperature (e.g., 800° C.). Specifically, the increase of the composite particle diameter and the value of weight loss at a high temperature are reduced. Moreover, a terminal perfluoroalkyl group having less than 8 carbon atoms do not lead to environmental pollution because they do not produce perfluorooctanoic acid and the like when released into the environment.

EMBODIMENTS FOR CARRYING OUT THE INVENTION

The fluorine-containing alcohol [I] is, for example, a polyfluoroalkyl alcohol represented by the general formula:

$$C_nF_{2n+1}(CH_2)_j\text{OH} \quad [II]$$

n: 1 to 10, preferably 1 to 6
j: 1 to 6, preferably 2

The alkylene group A is, for example, a —$CH_2$— group, —$CH_2CH_2$— group, or the like. Examples of perfluoroalkyl alcohols having such an alkylene group include 2,2,2-trifluoroethanol ($CF_3CH_2OH$), 3,3,3-trifluoropropanol ($CF_3CH_2CH_2OH$), 2,2,3,3,3-pentafluoropropanol ($CF_3CF_2CH_2OH$), 3,3,4,4,4-pentafluorobutanol ($CF_3CF_2CH_2CH_2OH$), 2,2,3,3,4,4,5,5,5-nonafluoropentanol ($CF_3CF_2CF_2CF_2CH_2OH$), 3,3,4,4,5,5,6,6,6-nonafluorohexanol ($CF_3CF_2CF_2CF_2CH_2CH_2OH$), 3,3,4,4,5,5,6,6,7,7,8,8,8-tridecafluorooctanol ($CF_3CF_2CF_2CF_2CF_2CF_2CH_2CH_2OH$), and the like.

Moreover, a polyfluoroalkyl group refers to a group in which the terminal —$CF_3$ group of a perfluoroalkyl group is replaced by, for example, a —$CF_2H$ group. Examples thereof include 2,2,3,3-tetrafluoropropanol ($HCF_2CF_2CH_2OH$), 2,2,3,4,4,4-hexafluorobutanol ($CF_3CHFCF_2CH_2OH$), 2,2,3,3,4,4,5,5-octafluoropentanol ($HCF_2CF_2CF_2CF_2CH_2OH$), and the like.

The polyfluoroalkyl alcohol represented by the general formula [II] is described, for example, in Patent Document 2, and is synthesized through the following series of steps.

First, a polyfluoroalkyl iodide represented by the general formula:

$$C_nF_{2n+1}(CF_2CF_2)_b(CH_2CH_2)_cI$$

is reacted with N-methylformamide $HCONH(CH_3)$ to form a mixture of polyfluoroalkyl alcohol and its formate. Then, the mixture is hydrolyzed in the presence of an acid catalyst, thereby forming a polyfluoroalkyl alcohol of the formula:

$$C_nF_{2n+1}(CF_2CF_2)_b(CH_2CH_2)_cOH$$

Examples of the polyfluoroalkyl iodide include the following:

$CF_3(CH_2CH_2)I$
$CF_3(CH_2CH_2)_2I$
$C_2F_5(CH_2CH_2)I$
$C_2F_5(CH_2CH_2)_2I$
$C_3F_7(CH_2CH_2)I$
$C_3F_7(CH_2CH_2)_2I$
$C_4F_9(CH_2CH_2)I$
$C_4F_9(CH_2CH_2)_2I$
$C_2F_5(CF_2CF_2)(CH_2CH_2)I$
$C_2F_5(CF_2CF_2)(CH_2CH_2)_2I$
$C_2F_5(CF_2CF_2)_2(CH_2CH_2)I$
$C_2F_5(CF_2CF_2)_2(CH_2CH_2)_2I$
$C_2F_5(CF_2CF_2)_3(CH_2CH_2)I$
$C_4F_9(CF_2CF_2)(CH_2CH_2)I$
$C_4F_9(CF_2CF_2)_2(CH_2CH_2)I$
$C_4F_9(CF_2CF_2)(CH_2CH_2)_2I$
$C_4F_9(CF_2CF_2)_2(CH_2CH_2)_2I$
$C_4F_9(CF_2CF_2)_3(CH_2CH_2)I$

The fluorine-containing alcohol [I] may also be a fluorine-containing alcohol wherein the $R_F$ group is a polyfluoroalkyl group having 3 to 20 carbon atoms, preferably 6 to 10 carbon atoms, and A is an alkylene group having 1 to 6 carbon atoms, preferably 2 carbon atoms. Examples thereof include a polyfluoroalkyl alcohol represented by the general formula:

$$C_nF_{2n+1}(CH_2CF_2)_a(CF_2CF_2)_b(CH_2CH_2)_cOH \qquad [III]$$

n: 1 to 6, preferably 2 to 4
a: 1 to 4, preferably 1
b: 0 to 3, preferably 1 or 2
c: 1 to 3, preferably 1

The polyfluoroalkyl alcohol represented by the general formula [III] is disclosed in Patent Document 2, and synthesized through the following series of steps.

First of all, a polyfluoroalkyl iodide represented by the general formula:

$$C_nF_{2n+1}(CH_2CF_2)_a(CF_2CF_2)_b(CH_2CH_2)_cI$$

is reacted with N-methylformamide $HCONH(CH_3)$ to form a mixture of polyfluoroalkyl alcohol and its formate. The mixture is then subjected to a hydrolysis reaction in the presence of an acid catalyst to form a polyfluoroalkyl alcohol of the formula:

$$C_nF_{2n+1}(CH_2CF_2)_a(CF_2CF_2)_b(CH_2CH_2)_cOH$$

Examples of the polyfluoroalkyl iodide include the following:

$CF_3(CH_2CF_2)(CH_2CH_2)I$
$C_2F_5(CH_2CF_2)(CH_2CH_2)I$
$C_2F_5(CH_2CF_2)(CH_2CH_2)_2I$
$C_3F_7(CH_2CF_2)(CH_2CH_2)I$
$C_3F_7(CH_2CF_2)(CH_2CH_2)_2I$
$C_4F_9(CH_2CF_2)(CH_2CH_2)I$
$C_4F_9(CH_2CF_2)(CH_2CH_2)_2I$
$C_2F_5(CH_2CF_2)(CF_2CF_2)(CH_2CH_2)I$
$C_2F_5(CH_2CF_2)(CF_2CF_2)(CH_2CH_2)_2I$
$C_2F_5(CH_2CF_2)_2(CF_2CF_2)(CH_2CH_2)I$
$C_2F_5(CH_2CF_2)_2(CF_2CF_2)(CH_2CH_2)_2I$
$C_4F_9(CH_2CF_2)(CF_2CF_2)(CH_2CH_2)I$
$C_4F_9(CH_2CF_2)_2(CF_2CF_2)(CH_2CH_2)I$
$C_4F_9(CH_2CF_2)(CF_2CF_2)(CH_2CH_2)_2I$
$C_4F_9(CH_2CF_2)_2(CF_2CF_2)(CH_2CH_2)_2I$

The fluorine-containing alcohol [Ia] is, for example, a fluorine-containing alcohol wherein the $R_F'$ group is a perfluoroalkyl group having 3 to 305 carbon atoms, preferably 8 to 35 carbon atoms, and A is an alkylene group having 1 to 3 carbon atoms, preferably 1 carbon atom. Examples thereof include a hexafluoropropene oxide oligomer alcohol represented by the general formula:

$$C_mF_{2m+1}O[CF(CF_3)CF_2O]_dCF(CF_3)(CH_2)_eOH \qquad [IIa]$$

m: 1 to 3, preferably 3
d: 0 to 100, preferably 1 to 10
e: 1 to 3, preferably 1

Moreover, the fluorine-containing alcohol [Ib] may be a fluorine-containing alcohol wherein the $R_F''$ group is a perfluoroalkylene group having 5 to 160 carbon atoms, and A is an alkylene group having 1 to 3 carbon atoms, preferably 1 carbon atom. Examples thereof include a perfluoroalkylene ether diol represented by the general formula:

$$HO(CH_2)_fCF(CF_3)[OCF_2CF(CF_3)]_gO(CF_2)_hO[CF(CF_3)CF_2O]_iCF(CF_3)(CH_2)_jOH \qquad [IIb]$$

f: 1 to 3, preferably 1
g+i: 0 to 50, preferably 2 to 50
h: 1 to 6, preferably 2

Among hexafluoropropene oxide oligomer alcohols represented by the general formula [IIa], a compound wherein m is 1 and e is 1 is described in Patent Document 3, and synthesized through the following step.

A fluorine-containing ether carboxylic acid alkyl ester represented by the general formula: $CF_3O[CF(CF_3)CF_2O]_n$ $CF(CF_3)COOR$ (R: an alkyl group, n: an integer of 0 to 12) is subjected to a reduction reaction using a reducing agent, such as sodium boron hydride.

Moreover, a perfluoroalkylene ether diol represented by the general formula [IIc] wherein f=1 is disclosed in Patent Documents 4 and 5, and synthesized via the following series of steps:

$$FOCR_fCOF \rightarrow H_3COOCR_fCOOCH_3 \rightarrow HOCH_2R_fCH_2OH$$

Rf: —$C(CF_3)[OCF_2C(CF_3)]_aO(CF_2)_cO[CF(CF_3)CF_2O]_bCF(CF_3)$—

Such a fluorine-containing alcohol and an alkoxysilane are reacted in the presence of an alkaline or acidic catalyst, thereby forming fluorine-containing nano composite particles.

The alkoxysilane is represented by the general formula:

$$(R_1O)_pSi(OR_2)_q(R_3)_r \qquad [IV]$$

$R_1$, $R_3$: H, $C_1$-$C_6$ alkyl group, or aryl group
$R_2$: $C_1$-$C_6$ alkyl group or aryl group,
  with the proviso that not all of $R_1$, $R_2$, and $R_3$ are aryl groups
p+q+r: 4, with the proviso that q is not 0
and examples thereof include trimethoxysilane, triethoxysilane, trimethoxymethylsilane, triethoxymethylsilane, trimethoxyphenylsilane, triethoxyphenylsilane, tetramethoxysilane, tetraethoxysilane, and the like.

The proportion of these components is such that about 10 to 200 parts by weight, preferably about 50 to 150 parts by weight, of alkoxysilane is used based on 100 parts by weight of fluorine-containing alcohol. When the amount of alkoxysilane used is less than this range, dispersibility into a solvent becomes poor. In contrast, when the amount of alkoxysilane used is greater than this range, water- and oil-repellency is deteriorated.

The reaction between these components is performed in the presence of an alkaline or acid catalyst, such as aqueous ammonia, an aqueous solution of a hydroxide of an alkali metal or alkaline earth metal (e.g., sodium hydroxide, potassium hydroxide, or calcium hydroxide), hydrochloric acid, or sulfuric acid, at a temperature of about 0 to 100° C., preferably about 10 to 30° C., for about 0.5 to 48 hours, preferably about 1 to 10 hours.

The amount of fluorine-containing alcohol in the obtained fluorine-containing nano composite particles is about 1 to 50 mol %, preferably about 5 to 30 mol %. The composite particle size (measured by a dynamic light scattering method) is about 30 to 200 nm.

In the production of such a fluorine-containing nano composite, when a condensation reaction is performed by making organo nano-silica particles coexist in the reaction system, fluorine-containing nano-silica composite particles can be produced as a condensate comprising three components, i.e., a fluorine-containing alcohol, an alkoxysilane, and nano-silica particles.

EXAMPLES

The following describes the present invention with reference to Examples.

Reference Example 1

$CF_3(CF_2)_3(CH_2)_2OH$ [FA-4] (0.25 g) was added and dissolved in 30 ml of methanol. To the resulting solution, 1.67 g (0.50 g as nano-silica) of silica sol (Methanol Silica Sol, a product of Nissan Chemical Industries, Ltd.; nano-silica content: 30 wt. %, average particle diameter: 11 nm) and 0.25 ml of tetraethoxysilane (a product of Tokyo Chemical Industry Co., Ltd.; density: 0.93 g/ml) were added. While stirring the mixture with a magnetic stirrer, 0.25 ml of 25 wt. % aqueous ammonia was added, and the mixture was reacted for 5 hours.

After completion of the reaction, the methanol and aqueous ammonia were removed using an evaporator under reduced pressure, and the resulting powder was redispersed in approximately 20 ml of methanol overnight. The next day, centrifugation was performed using a centrifuge tube, the supernatant was removed, and fresh methanol was added to perform rinsing. After rinsing was performed 3 times, the opening of the centrifuge tube was covered with aluminum foil, and the tube was placed in an oven at 70° C. overnight. The next day, the tube was placed and dried in a vacuum dryer at 50° C. overnight, thereby obtaining 0.582 g (yield: 71%) of white powder.

The particle size of the obtained white powdery fluorine-containing nano-silica composite particles, and the variation of the particle size were measured in a methanol dispersion having a solid matters content of 1 g/L at 25° C. by a dynamic light scattering (DLS) measurement method. Further, thermogravimetric analysis (TGA) was performed before calcining and after calcining up to 800° C. The heating rate in this case was 10° C./min. Moreover, the percentage of the weight loss due to calcining with respect to the initial weight was also calculated.

Further, the dispersibility of the composite particles dispersed with a solid matters content of 1 wt. % in water [$H_2O$], methanol [MeOH], ethanol [EtOH], 1,2-dichloroethane [DCE], and tetrahydrofuran [THF] was visually observed, and the results were evaluated according to the following evaluation criteria.

◯: Uniformly dispersed, transparent dispersion
Δ: Slightly dispersed, cloudy dispersion
×: Not dispersed, precipitated in dispersion medium

Reference Examples 2 to 5

In Reference Example 1, the amount of 25 wt. % aqueous ammonia was variously changed.

Reference Examples 6 to 10

In Reference Examples 1 to 5, the same amount (0.25 g) of $CF_3(CF_2)_5(CH_2)_2OH$ [FA-6; $C_2F_5(CF_2CF_2)_2(CH_2CH_2)OH$] was used as the fluorine-containing alcohol.

Reference Examples 11 to 15

In Reference Examples 1 to 5, the same amount (0.25 g) of $CF_3(CF_2)_7(CH_2)_2OH$ [FA-8; $C_2F_5(CF_2CF_2)_3(CH_2CH_2)OH$] was used as the fluorine-containing alcohol.

Reference Examples 16 to 20

In Reference Examples 1 to 5, the same amount (0.25 g) of $CF_3(CF_2)_3CH_2(CF_2)_5(CH_2)_2OH$ [DTFA; $C_4F_9(CH_2CF_2)(CF_2CF_2)_2(CH_2CH_2)OH$] was used as the fluorine-containing alcohol.

Reference Examples 21 to 25

In Reference Example 2, the same amount (0.25 g) of each of the following compounds was used as the fluorine-containing alcohol.

Ref. Ex.21: $CF_3(CF_2)_2OCF(CF_3)CF_2OCF(CF_3)CH_2OH$ [PO-3-OH]
Ref. Ex.22: $CF_3(CF_2)_2O[CF(CF_3)CF_2O]_4CF(CF_3)CH_2OH$ [PO-6-OH]
Ref. Ex.23: $HOCH_2[CF(CF_3)OCF_2]_2CF_2OCF(CF_3)CH_2OH$ [OXF3PO—OH]
Ref. Ex.24: $HOCH_2CF(CF_3)[OCF_2CF(CF_3)]_nOCF_2CF_2O[CF(CF_3)CF_2O]_m$—$CF(CF_3)CH_2OH$(n+m=6) [OXF8PO—OH]
Ref. Ex.25: $HOCH_2CF(CF_3)[OCF_2CF(CF_3)]_nOCF_2CF_2O[CF(CF_3)CF_2O]_m$—$CF(CF_3)CH_2OH$(n+m=12) [OXF14PO—OH]

Table 1 below shows the amount of aqueous ammonia, recovered amount, yield, and various measurement results in the above Reference Examples. Further, Table 2 shows the evaluation of dispersibility.

The yield was calculated by the following formula on the assumption that tetraalkoxysilane underwent a self-condensation reaction to form three-dimensional siloxane bonds Si—O and generate a —O—Si—O— [$SiO_2$] skeleton among them. When silica is not used, the yield is calculated based on C=0.

$$\text{Yield (\%)} = A/[B+C+(D \times E \times F/G)] \times 100$$

A: weight of produced composite (g)
B: weight of fluorine-containing alcohol (g)
C: weight of silica (g)
D: volume of tetraalkoxysilane (ml)
E: density of tetraalkoxysilane (g/ml)
F: molar weight (g/mol) of $SiO_2$ derived from tetraalkoxysilane
G: molar weight (g/mol) of tetraalkoxysilane

TABLE 1

| Reference Ex. | aq. NH₃ (ml) | Recovery amount(g) | Yield (%) | Fluorine-containing nano-silica composite particle size (nm) | | Weight loss(%) |
|---|---|---|---|---|---|---|
| | | | | Before calcining | After calcining up to 800° C. | |
| 1 | 0.25 | 0.582 | 71 | 36.8 ± 9.9 | 39.0 ± 3.1 | 7 |
| 2 | 0.50 | 0.559 | 68 | 30.1 ± 7.3 | 39.5 ± 9.9 | 7 |
| 3 | 1.0 | 0.352 | 43 | 69.1 ± 13.9 | 45.3 ± 10.9 | 7 |
| 4 | 2.0 | 0.419 | 51 | 41.5 ± 10.2 | 42.6 ± 9.2 | 7 |
| 5 | 4.0 | 0.571 | 70 | 34.0 ± 7.6 | 139.8 ± 25.5 | 7 |
| 6 | 0.25 | 0.500 | 61 | 35.3 ± 8.3 | 53.3 ± 11.4 | 8 |
| 7 | 0.50 | 0.580 | 71 | 40.5 ± 11.3 | 40.5 ± 12.0 | 6 |
| 8 | 1.0 | 0.590 | 72 | 40.5 ± 13.0 | 62.3 ± 18.5 | 6 |
| 9 | 2.0 | 0.488 | 60 | 105.3 ± 19.0 | 97.5 ± 30.2 | 7 |
| 10 | 4.0 | 0.426 | 52 | 45.4 ± 13.2 | 60.9 ± 17.1 | 6 |
| 11 | 0.25 | 0.521 | 64 | 41.7 ± 13.7 | 81.7 ± 21.6 | 7 |
| 12 | 0.50 | 0.481 | 59 | 28.2 ± 6.0 | 32.2 ± 9.8 | 6 |
| 13 | 1.0 | 0.475 | 58 | 56.6 ± 11.5 | 53.7 ± 10.2 | 6 |
| 14 | 2.0 | 0.516 | 63 | 53.6 ± 11.4 | 55.1 ± 14.5 | 6 |
| 15 | 4.0 | 0.565 | 69 | 39.7 ± 9.2 | 35.4 ± 12.8 | 7 |
| 16 | 0.25 | 0.580 | 71 | 54.5 ± 19.3 | 71.9 ± 15.3 | 7 |
| 17 | 0.50 | 0.604 | 74 | 44.3 ± 13.8 | 46.2 ± 10.4 | 7 |
| 18 | 1.0 | 0.523 | 64 | 55.6 ± 12.3 | 53.1 ± 14.7 | 8 |
| 19 | 2.0 | 0.504 | 62 | 53.6 ± 10.3 | 54.0 ± 12.9 | 6 |
| 20 | 4.0 | 0.578 | 71 | 63.6 ± 14.1 | 72.0 ± 15.5 | 6 |
| 21 | 0.5 | 0.556 | 68 | 42.2 ± 4.2 | 35.2 ± 8.4 | 5 |
| 22 | 0.5 | 0.580 | 71 | 130.5 ± 27.5 | 29.8 ± 5.8 | 7 |
| 23 | 0.5 | 0.466 | 57 | 55.5 ± 7.9 | 23.7 ± 7.1 | 5 |
| 24 | 0.5 | 0.359 | 44 | 96.9 ± 10.9 | 30.0 ± 6.9 | 11 |
| 25 | 0.5 | 0.507 | 62 | 90.8 ± 14.8 | 47.2 ± 9.7 | 20 |

TABLE 2

| Ex. | H₂O | MeOH | EtOH | DCE | THF |
|---|---|---|---|---|---|
| Ref. Ex. 1 | Δ | ○ | ○ | ○ | ○ |
| Ref. Ex. 2 | Δ | ○ | ○ | ○ | ○ |
| Ref. Ex. 3 | ○ | ○ | ○ | ○ | ○ |
| Ref. Ex. 4 | ○ | ○ | ○ | ○ | ○ |
| Ref. Ex. 5 | ○ | ○ | ○ | ○ | ○ |
| Ref. Ex. 6 | ○ | ○ | ○ | ○ | ○ |
| Ref. Ex. 7 | ○ | ○ | ○ | ○ | ○ |
| Ref. Ex. 8 | Δ | ○ | ○ | ○ | ○ |
| Ref. Ex. 9 | ○ | ○ | ○ | ○ | ○ |
| Ref. Ex. 10 | ○ | ○ | ○ | ○ | ○ |
| Ref. Ex. 11 | ○ | ○ | ○ | ○ | ○ |
| Ref. Ex. 12 | ○ | ○ | ○ | ○ | ○ |
| Ref. Ex. 13 | ○ | ○ | ○ | ○ | ○ |
| Ref. Ex. 14 | ○ | ○ | ○ | ○ | ○ |
| Ref. Ex. 15 | ○ | ○ | ○ | ○ | ○ |
| Ref. Ex. 16 | ○ | ○ | ○ | ○ | ○ |
| Ref. Ex. 17 | ○ | ○ | ○ | ○ | ○ |
| Ref. Ex. 18 | ○ | ○ | ○ | ○ | ○ |
| Ref. Ex. 19 | ○ | ○ | ○ | ○ | ○ |
| Ref. Ex. 20 | ○ | ○ | ○ | ○ | ○ |
| Ref. Ex. 21 | ○ | ○ | ○ | ○ | ○ |
| Ref. Ex. 22 | ○ | ○ | ○ | ○ | ○ |
| Ref. Ex. 23 | ○ | ○ | ○ | ○ | ○ |
| Ref. Ex. 24 | ○ | ○ | ○ | ○ | ○ |
| Ref. Ex. 25 | ○ | ○ | ○ | ○ | ○ |

Examples 1 to 3

In Reference Examples 13 to 15, methanol silica sol was not used.

Examples 4 to 6

In Reference Examples 18 to 20, methanol silica sol was not used.

Examples 7 to 9

In Reference Example 21, methanol silica sol was not used, and the amount of 25% aqueous ammonia was variously changed.

Examples 10 to 12

In Reference Example 22, methanol silica sol was not used, and the amount of 25% aqueous ammonia was variously changed.

Example 13

In Reference Example 23, methanol silica sol was not used, and the amount of 25% aqueous ammonia was changed to 4.0 ml.

Example 14

In Reference Example 24, methanol silica sol was not used, and the amount of 25% aqueous ammonia was changed to 4.0 ml.

Example 15

In Reference Example 25, methanol silica sol was not used, and the amount of 25% aqueous ammonia was changed to 4.0 ml.

Table 3 below shows the amount of aqueous ammonia, recovered amount, yield, and various measurement results in the above Examples. Further, Table 4 shows the evaluation of dispersibility.

TABLE 3

| Ex. | aq. NH₃ (ml) | Recovery amount(g) | Yield (%) | Fluorine-containing nano composite particle size (nm) Before calcining | After calcining up to 800° C. | Weight loss(%) |
|---|---|---|---|---|---|---|
| 1 | 1.0 | 0.065 | 20 | 54.5 ± 12.0 | 16.6 ± 3.8 | 18 |
| 2 | 2.0 | 0.059 | 19 | 21.1 ± 6.0 | 26.4 ± 6.0 | 17 |
| 3 | 4.0 | 0.065 | 20 | 37.3 ± 8.1 | 49.6 ± 11.2 | 17 |
| 4 | 1.0 | 0.072 | 23 | 41.0 ± 8.7 | 16.3 ± 3.9 | 17 |
| 5 | 2.0 | 0.044 | 14 | 47.5 ± 10.1 | 24.4 ± 5.7 | 20 |
| 6 | 4.0 | 0.069 | 22 | 81.5 ± 14.5 | 24.2 ± 5.6 | 25 |
| 7 | 1.0 | 0.073 | 23 | 48.3 ± 4.8 | 34.2 ± 4.4 | 16 |
| 8 | 2.0 | 0.073 | 23 | 53.1 ± 5.1 | 38.0 ± 9.2 | 12 |
| 9 | 4.0 | 0.067 | 21 | 45.1 ± 6.5 | 51.1 ± 16.8 | 12 |
| 10 | 1.0 | 0.070 | 22 | 141.5 ± 31.8 | 26.6 ± 6.3 | 16 |
| 11 | 2.0 | 0.048 | 15 | 80.2 ± 31.2 | 80.5 ± 21.2 | 13 |
| 12 | 4.0 | 0.063 | 20 | 69.2 ± 10.1 | 69.4 ± 12.5 | 12 |
| 13 | 4.0 | 0.051 | 16 | 60.5 ± 12.4 | 55.1 ± 12.1 | 12 |
| 14 | 4.0 | 0.063 | 20 | 55.7 ± 8.9 | 65.4 ± 12.1 | 13 |
| 15 | 4.0 | 0.171 | 54 | 63.2 ± 6.7 | 53.5 ± 7.8 | — |

TABLE 4

| Ex. | H₂O | MeOH | EtOH | DCE | THF |
|---|---|---|---|---|---|
| 1 | ○ | ○ | ○ | ○ | ○ |
| 2 | ○ | ○ | ○ | ○ | ○ |
| 3 | Δ | ○ | ○ | ○ | ○ |
| 4 | ○ | ○ | ○ | ○ | ○ |
| 5 | ○ | ○ | ○ | ○ | ○ |
| 6 | ○ | ○ | ○ | ○ | ○ |
| 7 | ○ | ○ | ○ | ○ | ○ |
| 8 | ○ | ○ | ○ | ○ | ○ |
| 9 | ○ | ○ | ○ | ○ | ○ |
| 10 | ○ | ○ | ○ | ○ | ○ |
| 11 | Δ | ○ | ○ | ○ | ○ |
| 12 | ○ | ○ | ○ | ○ | ○ |
| 13 | ○ | ○ | ○ | ○ | ○ |
| 14 | Δ | ○ | ○ | ○ | ○ |
| 15 | ○ | ○ | ○ | ○ | ○ |

Reference Examples 31 to 55

Prepared glass slides were dipped in methanol dispersions (particle concentration: 5 g/L) of the fluorine-containing nano-silica composite particles before calcining obtained in Reference Examples 1 to 25, and then dried at room temperature. Droplets (4 μl) were gently brought into contact with the obtained thin layer surfaces at room temperature, and the contact angle (unit: °) of the droplets adhering to n-dodecane or water was measured by the θ/2 method using a contact angle meter (Drop Master 300, produced by Kyowa Interface Science Co., Ltd.). The contact angle with water was measured with time. Table 5 below shows the obtained results.

TABLE 5

| Example | Composite | Dodecane | Water (elapsed time: min.) | | | | | | |
|---|---|---|---|---|---|---|---|---|---|
| | | | 0 | 5 | 10 | 15 | 20 | 25 | 30 |
| Ref. Ex. 31 | Ref. Ex. 1 | 35 | 21 | 10 | 0 | 0 | 0 | 0 | 0 |
| Ref. Ex. 32 | Ref. Ex. 2 | 7 | 22 | 17 | 15 | 13 | 11 | 10 | 7 |
| Ref. Ex. 33 | Ref. Ex. 3 | 4 | 7 | 0 | 0 | 0 | 0 | 0 | 0 |
| Ref. Ex. 34 | Ref. Ex. 4 | 0 | 7 | 0 | 0 | 0 | 0 | 0 | 0 |
| Ref. Ex. 35 | Ref. Ex. 5 | 0 | 0 | 0 | 0 | 0 | 0 | 0 | 0 |
| Ref. Ex. 36 | Ref. Ex. 6 | 49 | 28 | 0 | 0 | 0 | 0 | 0 | 0 |
| Ref. Ex. 37 | Ref. Ex. 7 | 46 | 48 | 27 | 26 | 24 | 20 | 20 | 17 |
| Ref. Ex. 38 | Ref. Ex. 8 | 16 | 19 | 19 | 16 | 14 | 13 | 10 | 8 |
| Ref. Ex. 39 | Ref. Ex. 9 | 14 | 11 | 0 | 0 | 0 | 0 | 0 | 0 |
| Ref. Ex. 40 | Ref. Ex. 10 | 19 | 16 | 7 | 0 | 0 | 0 | 0 | 0 |
| Ref. Ex. 41 | Ref. Ex. 11 | 114 | 37 | 34 | 33 | 31 | 30 | 30 | 28 |
| Ref. Ex. 42 | Ref. Ex. 12 | 108 | 61 | 58 | 52 | 49 | 46 | 45 | 41 |
| Ref. Ex. 43 | Ref. Ex. 13 | 123 | 59 | 17 | 0 | 0 | 0 | 0 | 0 |
| Ref. Ex. 44 | Ref. Ex. 14 | 125 | 23 | 13 | 10 | 8 | 0 | 0 | 0 |
| Ref. Ex. 45 | Ref. Ex. 15 | 127 | 91 | 18 | 4 | 0 | 0 | 0 | 0 |
| Ref. Ex. 46 | Ref. Ex. 16 | 82 | 30 | 21 | 20 | 14 | 9 | 0 | — |
| Ref. Ex. 47 | Ref. Ex. 17 | 71 | 64 | 61 | 58 | 56 | 55 | 52 | 52 |
| Ref. Ex. 48 | Ref. Ex. 18 | 55 | 79 | 77 | 75 | 68 | 61 | 58 | 52 |
| Ref. Ex. 49 | Ref. Ex. 19 | 80 | 95 | 75 | 63 | 57 | 50 | 47 | 42 |
| Ref. Ex. 50 | Ref. Ex. 20 | 47 | 113 | 82 | 72 | 64 | 57 | 53 | 49 |
| Ref. Ex. 51 | Ref. Ex. 21 | 72 | 23 | 0 | 0 | 0 | 0 | 0 | 0 |
| Ref. Ex. 52 | Ref. Ex. 22 | 62 | 0 | 0 | 0 | 0 | 0 | 0 | 0 |
| Ref. Ex. 53 | Ref. Ex. 23 | 49 | 18 | 0 | 0 | 0 | 0 | 0 | 0 |
| Ref. Ex. 54 | Ref. Ex. 24 | 51 | 24 | 11 | 0 | 0 | 0 | 0 | 0 |
| Ref. Ex. 55 | Ref. Ex. 25 | 66 | 17 | 0 | 0 | 0 | 0 | 0 | 0 |

Examples 21 to 35

The contact angle of the fluorine-containing nano composite particles before calcining obtained in Examples 1 to 15 was measured in the same way as in Reference Examples 31 to 55. Table 6 below shows the obtained results.

TABLE 6

| Ex. | Composite | Dodecane | Water (elapsed time: min.) | | | | | | |
|---|---|---|---|---|---|---|---|---|---|
| | | | 0 | 5 | 10 | 15 | 20 | 25 | 30 |
| Ex. 21 | Ex. 1 | 50 | 52 | 48 | 45 | 38 | 34 | 29 | 25 |
| Ex. 22 | Ex. 2 | 45 | 62 | 54 | 47 | 44 | 37 | 33 | 25 |
| Ex. 23 | Ex. 3 | 43 | 35 | 29 | 26 | 22 | 18 | 14 | 9 |
| Ex. 24 | Ex. 4 | 98 | 81 | 69 | 61 | 57 | 53 | 50 | 44 |
| Ex. 25 | Ex. 5 | 73 | 86 | 69 | 51 | 45 | 36 | 28 | 22 |
| Ex. 26 | Ex. 6 | 43 | 61 | 51 | 48 | 44 | 36 | 29 | 24 |
| Ex. 27 | Ex. 7 | 42 | 27 | 17 | 17 | 15 | 15 | 14 | |
| Ex. 28 | Ex. 8 | 51 | 30 | 25 | 23 | 23 | 22 | 20 | 19 |
| Ex. 29 | Ex. 9 | 34 | 23 | 0 | 0 | 0 | 0 | 0 | 0 |
| Ex. 30 | Ex. 10 | 59 | 43 | 18 | 15 | 13 | 13 | 12 | 11 |
| Ex. 31 | Ex. 11 | 64 | 51 | 37 | 35 | 35 | 34 | 31 | 31 |
| Ex. 32 | Ex. 12 | 61 | 34 | 28 | 27 | 24 | 24 | 23 | 23 |
| Ex. 33 | Ex. 13 | 54 | 33 | 12 | 11 | 10 | 10 | 9 | 8 |
| Ex. 34 | Ex. 14 | 63 | 90 | 42 | 40 | 40 | 38 | 37 | 37 |
| Ex. 35 | Ex. 15 | 64 | 91 | 47 | 45 | 44 | 42 | 42 | 42 |

The invention claimed is:

1. Method for producing fluorine-containing nano composite particles, the method comprising subjecting a fluorine-containing alcohol represented by the general formula:

$$R_F\text{-A-OH} \quad [I]$$

wherein $R_F$ is a perfluoroalkyl group or a polyfluoroalkyl group in which some of the fluorine atoms of the perfluoroalkyl group are replaced by hydrogen atoms, and A is an alkylene group having 1 to 6 carbon atoms; and an alkoxysilane to a condensation reaction in the presence of an aqueous ammonia catalyst.

2. Method for producing fluorine-containing nano composite particles according to claim 1, wherein the fluorine-containing alcohol represented by the general formula [I] is a polyfluoroalkyl alcohol represented by the general formula:

$$C_nF_{2n+1}(CH_2)_j\text{OH} \quad [II]$$

wherein n is an integer of 1 to 10, and j is an integer of 1 to 6.

3. Method for producing fluorine-containing nano composite particles according to claim 1, wherein the fluorine-containing alcohol represented by the general formula [I] is a polyfluoroalkyl alcohol represented by the general formula:

$$C_nF_{2n+1}(CH_2CF_2)_a(CF_2CF_2)_b(CH_2CH_2)_cOH \quad [III]$$

wherein n is an integer of 1 to 6, a is an integer of 1 to 4, b is an integer of 0 to 3, and c is an integer of 1 to 3.

4. Method for producing fluorine-containing nano composite particles according to claim 1, wherein the alkoxysilane is a silane derivative represented by the general formula:

$$(R_1O)_pSi(OR_2)_q(R_3)_r \quad [IV]$$

wherein $R_1$ and $R_3$ are each a hydrogen atom, an alkyl group having 1 to 6 carbon atoms, or an aryl group; $R_2$ is an alkyl group having 1 to 6 carbon atoms or an aryl group, with the proviso that not all of $R_1$, $R_2$, and $R_3$ are aryl groups; and p+q+r is 4, with the proviso that q is not 0.

5. Method for producing fluorine-containing nano composite particles according to claim 1, wherein the fluorine-containing alcohol [I] and an alkoxysilane are subjected to a condensation reaction at a reaction temperature of 10 to 30° C.

6. Method for producing fluorine-containing nano composite particles, the method comprising subjecting a fluorine-containing alcohol represented by the general formula:

$$R_F'\text{-A-OH} \quad [Ia]$$

or the general formula:

$$\text{HO-A-}R_F''\text{-A-OH} \quad [Ib]$$

wherein $R_F'$ is a liner or branched perfluoroalkyl group containing an O, S, or N atom, $R_F''$ is a linear or branched perfluoroalkylene group containing an O, S, or N atom, and A is an alkylene group having 1 to 6 carbon atoms; and an alkoxysilane to a condensation reaction in the presence of an aqueous ammonia catalyst.

7. Method for producing fluorine-containing nano composite particles according to claim 6, wherein the fluorine-containing alcohol represented by the general formula [Ia] is a hexafluoropropene oxide oligomer alcohol represented by the general formula:

$$C_mF_{2m+1}O[CF(CF_3)CF_2O]_dCF(CF_3)(CH_2)_eOH \quad [IIa]$$

wherein m is an integer of 1 to 3, d is an integer of 0 to 100, and e is an integer of 1 to 3.

8. Method for producing fluorine-containing nano composite particles according to claim 6, wherein the fluorine-containing alcohol represented by the general formula [Ib] is a perfluoroalkylene ether diol represented by the general formula:

$$HO(CH_2)_fCF(CF_3)[OCF_2CF(CF_3)]_gO(CF_2)_hO[CF(CF_3)CF_2O]_iCF(CF_3)(CH_2)_fOH \quad [IIb]$$

wherein f is an integer of 1 to 3, g+i is an integer of 0 to 50, and h is an integer of 1 to 6.

9. Method for producing fluorine-containing nano composite particles according to claim 6, wherein the alkoxysilane is a silane derivative represented by the general formula:

$$(R_1O)_pSi(OR_2)_q(R_3)_r \quad [III]$$

wherein $R_1$ and $R_3$ are each a hydrogen atom, an alkyl group having 1 to 6 carbon atoms, or an aryl group; $R_2$ is an alkyl group having 1 to 6 carbon atoms or an aryl group, with the proviso that not all of $R_1$, $R_2$, and $R_3$ are aryl groups; and p+q+r is 4, with the proviso that q is not 0.

10. Method for producing fluorine-containing nano composite particles according to claim 6, wherein the fluorine-containing alcohol [Ia] or [Ib] and an alkoxysilane are subjected to a condensation reaction at a reaction temperature of 10 to 30° C.

11. Water- and oil-repellent comprising the fluorine-containing nano composite particles produced by the method according to claim 6 as an active ingredient.

* * * * *